United States Patent [19]

Demarne et al.

[11] 4,356,177

[45] Oct. 26, 1982

[54] MYOCARDIUM-PROTECTING PYRIDINE DERIVATIVES HAVING AN ANTI-ARRHYTHMIC ACTIVITY AND AN ACTIVITY AS BLOOD-PLATELETS ANTIAGGREGANTS

[75] Inventors: Henri Demarne, Montpellier; Claude Bernhart, Saint Gely du Fesc; Jacqueline Lansen, Montpellier, all of France

[73] Assignee: C.M. Industries, Paris, France

[21] Appl. No.: 194,829

[22] Filed: Oct. 7, 1980

[30] Foreign Application Priority Data

Oct. 11, 1979 [FR] France .................................. 79 25370

[51] Int. Cl.³ .................... A61K 31/535; C07D 413/06
[52] U.S. Cl. ............................... 424/248.54; 424/263; 424/267; 544/131; 546/193; 546/194; 546/275; 546/281; 546/333; 546/336; 546/337
[58] Field of Search ............... 546/193, 194, 275, 281, 546/333, 336, 337; 544/131; 424/267, 263, 248.54

[56] References Cited

U.S. PATENT DOCUMENTS 4,107,207 8/1978 Rengarger et al. .................. 546/336

FOREIGN PATENT DOCUMENTS 948860 2/1964 United Kingdom ................ 546/337

OTHER PUBLICATIONS

Chemical Abstracts, vol. 91, Item 175,147j (1980) Abstracting CZUBA et al., "Pol. J. Pharmacol. Pharm." (1979), vol. 31, No. 1. pp. 59-63 (Eng.).

Primary Examiner—Robert T. Bond
Attorney, Agent, or Firm—Lewis H. Eslinger

[57] ABSTRACT

The present invention relates to new pyridine derivatives of formula:

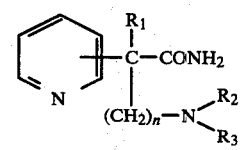

wherein $R_1$ is an alkyl or an alicyclic group, $R_2$ and $R_3$ are alkyls or alicyclic groups or form an heterocycle with the atom of nitrogen to which they are bonded; the invention also relates to a process for the preparation of said derivatives and the medicines containing at least one of the said derivatives.

23 Claims, No Drawings

MYOCARDIUM-PROTECTING PYRIDINE DERIVATIVES HAVING AN ANTI-ARRHYTHMIC ACTIVITY AND AN ACTIVITY AS BLOOD-PLATELETS ANTIAGGREGANTS

The present invention relates to pyridine derivatives as new industrial products, and to their preparation method and application in therapeutics.

The new compounds according to the invention are of general formula:

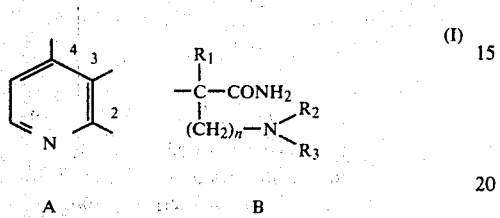

wherein:
the group B substitutes pyridine in position 2, 3, or 4;
$R_1$ is a straight or branched alkyl group or unsaturated alkyl group, i.e., alkenyl or alkynyl with between 1 and 10 carbon atoms or an alicyclic group;
$R_2$ and $R_3$ are a straight or branched alkyl group of 1 to 6 carbon atoms or an alicyclic group or else the two groups $R_2$ and $R_3$ with the nitrogen atom to which they are bonded constitute a 5- to 7 membered heterocyclic which may contain a second heteroatom and one or more substituents, in particular 1 or more alkyl groups;
n is 2, 3 or 4.

The compounds (I) give soluble salts with organic or mineral acids. The compounds are derivatives of the corresponding carboxylic acids.

The compounds according to the invention are obtained according to either one of the following reaction diagrams:

METHOD A:

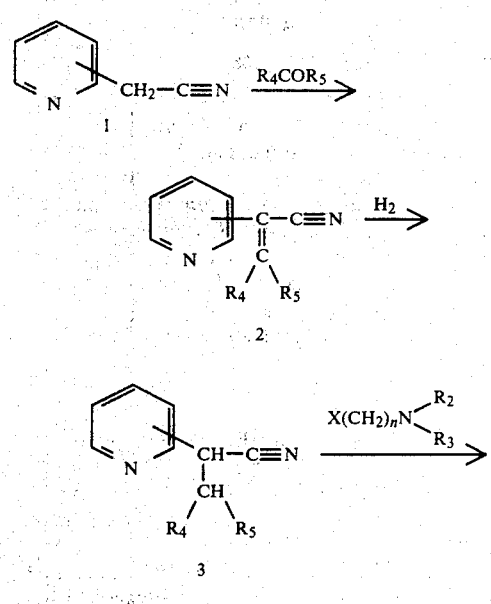

-continued
METHOD A:

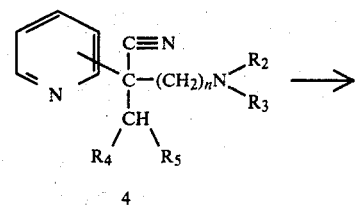

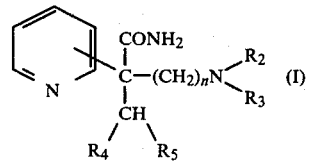

Acetontrile pyridyl 1, treated with an aldehyde or a ketone $R_4CO\ R_5$ ($R_4$=H or alkyl, $R_5$=alkyl) in the presence of acetic acid and piperidine, gives ethylenic nitrile 2. This is catalytically reduced into saturated nitrile 3. The latter, when subjected to an alkylation reaction with a halogen chain

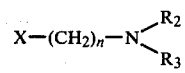

(X=halogen) leads to the compound 4 whose nitrile function is hydrolysed into amide to arrive at compound I.

By proper selection of radicals $R_4$ and $R_5$ of the aldehyde or ketone used for preparing 2, it is possible to obtain in the final compound I, straight, cyclic or ramified saturated radicals $R_1$.

METHOD B:

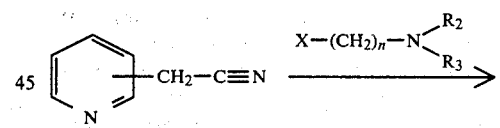

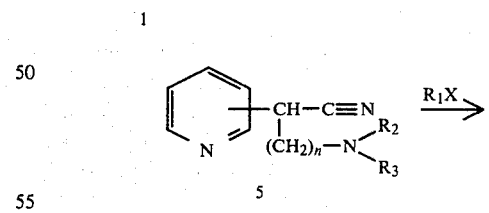

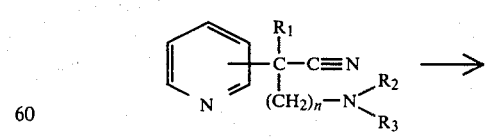

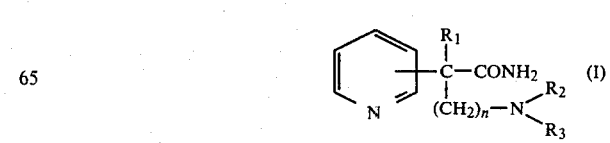

Acetontrile pyridyl 1 is first subjected to an alkylation reaction in the presence of a halogen chain:

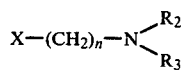

(X=halogen) to arrive at nitril 5.

The latter is then subjected to a second alkylation reaction in the presence of a compound $R_1X$ (X=halogen), thus giving nitrile 6. The compounds are eventually obtained by hydrolysing the nitrile in the presence of potassium in a hydro-alcoholic medium.

The following examples are given to illustrate the preparation of the compounds (I) according to method A or method B.

EXAMPLE I (Method A):

2-(2-diisopropylamino ethyl) 2-(2-pyridyl) 4-methyl pentanamide (CM 7857)

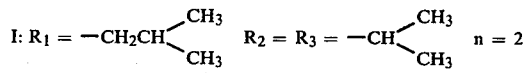

(a) 4-methyl 2-(2-pyridyl) 2-pentene nitrile.

In a flask equipped with a water separator are placed 7 g of 2-pyridyl acetonitrile, 12.8 g of isobutyraldehyde, 0.9 ml of acetic acid, 0.18 ml of piperidine and 250 ml of dry benzene. The mixture is heated under reflux for 3 hours. After cooling, the reaction mixture is washed with water, the organic phase is dried over sodium sulfate then the solvent is evaporated to dryness.

By distillating the residue, a yellow liquid is obtained (9.9 g); B.P./1.4 mm Hg: 89°–92° C.

(b) 4-methyl 2-(2-pyridyl) pentane nitrile

A solution of 9 g of the compound obtained above, dissolved in 100 ml of ethanol at 96° is hydrogenized at room temperature and pressure, in the presence of 3.8 g of palladium on charcoal at 5%. The reaction mixture is filtered and the filtrate is evaporated to dryness.

A yellow liquid is obtained (9 g) which is used for the following step.

(c) 2-(2-diisopropylamino ethyl) 2-(2-pyridyl) 4-methyl pentane nitrile.

A mixture of the 9 g of nitrile obtained above, with 9.3 g of 1-chloro 2-diisopropylaminoethane and 2.2 g of sodium amide sprayed in 150 ml of dry toluene is heated under reflux for two hours. The reaction mixture is washed in water, then the organic phase is dried over sodium sulfate and evaporated to dryness.

An orange-colored liquid (15.1 g) is obtained and used as such in the following step.

(d) CM 7857

15.1 g of the compound obtained above are heated for one hour in 100 ml of sulfuric acid d=1.83. After cooling, the solution is poured under stirring over 600 g of crushed ice. The mixture is alkalized with a solution of soda at 40% and extracted with chloroform. The organic phase is dried over sodium sulfate and the solvent is evaporated to dryness. The residue is separated by partition chromatography on an alumina column, eluting with a mixture of pentane and ethyl acetate.

A colorless solid is obtained (6.9 g).

After re-crystallizing in isopropylic ether the M.P. is 107°–108° C.

EXAMPLE 2

(Method B)

2-(2-diisopropylaminoethyl) 2-(2-pyridyl) 4-methyl 4-pentene amide (CM 40348)

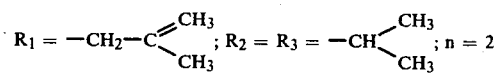

(a) 4-diiospropylamino2-(2-pyridyl) butanenitrile.

8 g of 2-pyridyl acetonitrile, 8.81 g of 1-chloro 2-diisopropylaminoethane and 0.27 g of benzyl triethyl ammonium chloride are placed in a flask. Keeping the temperature to below 35° C., 35 cm³ of soda at 50% are added. The mixture is heated to 35° C. for 5 hours. After returning to room temperature the mixture is diluted with water and extracted with ether. The organic phase is dried over sodium sulfate and the solvent is evaporated to dryness.

By distillating the residue, a yellow liquid is obtained (9.36 g); B.P./0.6 mm Hg: 132°–134° C.

(b) 2-(2-diisopropylaminoethyl) 2-(2-pyridyl) 4-methyl 4-pentene nitrile.

In a three-necked flask under nitrogen atmosphere are placed 1.5 g of sodium hydride (dispersion at 55-60% in oil) and 60 ml of dimethylformamide (DMF). 7.35 g of the above nitrile dissolved in 30 ml of DKF are added dropwise at room temperature. The mixture is stirred for 30 minutes at room temperature, then 3 g of 2-methyl 3-chloropropene dissolved in 30 ml of DMF are added. The mixture is stirred for one hour at room temperature and the DMF is evaporated under reduced pressure. The residue is taken up with water and extracted with ether. The organic phase is dried over sodium sulfate then evaporated to dryness.

An orange-colored liquid (10.2 g) is obtained which is used as such in the following step.

(c) CM 40348

10.2 g of the compound obtained above, 36 g of potassium, 150 ml of ethanol at 95% and 200 ml of water are heated under reflux for 86 hours. The alcohol is evaporated and the mixture is extracted with ethyl acetate. The organic phase is dried over sodium sulfate and the solvent is evaporated to dryness. The residue is separated by partition chromatography on an alumina column, eluting first with a mixture of pentane and ethyl acetate, and then with ethyl acetate. 4.73 g of white solid is obtained which is recrystallized in hexane. M.P. 92°–93° C.

EXAMPLES 3 to 22:

By operating according to method A, but by varying the starting acetonitrile pyridyl and/or the carbonyl-containing reagent $R_4COR_5$ used in the first step and/or the halogen chain used in the third step, the compounds I, listed in Table I are obtained.

The compounds of the invention have been examined in human and animal pharmacology particularly with a view to showing their anti-arrhythmic properties as well as their properties as blood-platelets anti-aggregants.

TABLE I

| Code No. | Substitution position on pyridine | $R_1$ | n | $-N{<}^{R_2}_{R_3}$ | Melting point (Crystallizing solvent) |
|---|---|---|---|---|---|
| 7526 | 2 | —cyclohexyl | 2 | $-N(CH(CH_3)_2)_2$ | 104–105 (isopropylic ether) |
| 7641 | 2 | $-CH(CH_3)_2$ | 2 | " | 85–86 (isopropylic ether) |
| 7827 | 2 | $-CH(CH_3)-CH_2CH_3$ | 2 | " | 90–91 (isopropylic ether) |
| 7828 | 2 | $-CH_2CH_3$ | 2 | " | 93–94 (isopropylic ether) |
| 7855 | 2 | $-CH(CH_2CH_3)_2$ | 2 | " | 62–63 (ethanol at 96°) |
| 7927 | 2 | $-CH_2CH_2CH_3$ | 2 | " | 87–88 (isopropylic ether) |
| 7973 | 2 | $-CH_2CH_2CH_2CH_2CH_3$ | 2 | " | 90–91 (isopropylic ether) |
| 7956 | 2 | $-CH_2$—cyclohexyl | 2 | " | 117 (isopropylic ether) |
| 7974 | 2 | $-CH_2-CH(CH_3)_2$ | 2 | 2,6-dimethylpiperidino | 119–120 (isopropylic ether) |
| 7975 | 2 | " | 2 | $-N(C_2H_5)_2$ | 78–79 (hexane) |
| 7976 | 2 | $-CH_2-CH_2-CH(CH_3)_2$ | 2 | $-N(CH(CH_3)_2)_2$ | 108–109 (isopropylic ether) |
| 40003 | 2 | $-CH_2-CH(CH_3)-CH_3$ | 2 | morpholino | 89–90 (isopropylic ether) |
| 40023 | 2 | $-CH_2-C(CH_3)_3$ | 2 | $-N(CH(CH_3)_2)_2$ | 103–104 (isopropylic ether) |
| 40156 | 2 | $-CH_2-CH(CH_3)_2$ | 2 | $-N(CH(CH_3)_2)(cyclohexyl)$ | 106–107 (isopropylic ether) |

TABLE I-continued

| Code No. | Substitution position on pyridine | $R_1$ | n | $-N\begin{smallmatrix}R_2\\R_3\end{smallmatrix}$ | Melting point (Crystallizing solvent) |
|---|---|---|---|---|---|
| 40163 | 2 | $-CH_2-CH_2-CH\begin{smallmatrix}CH_3\\CH_3\end{smallmatrix}$ | 2 | $-N\begin{smallmatrix}CH(CH_2-CH_3)(CH_3)\\CH(CH_3)(CH_2-CH_3)\end{smallmatrix}$ | 92-93 (isopropylic ether) |
| 40165 | 2 | $-CH_2-CH\begin{smallmatrix}CH_3\\CH_3\end{smallmatrix}$ | 2 | $-N\begin{smallmatrix}CH_2-CH_2-CH_3\\CH_2-CH_2-CH_3\end{smallmatrix}$ | 74-76 (isopropylic ether) |
| 40196 | 2 | $-CH_2-CH\begin{smallmatrix}CH_3\\CH_3\end{smallmatrix}$ | 3 | $-N\begin{smallmatrix}CH(CH_3)(CH_3)\\CH(CH_3)(CH_3)\end{smallmatrix}$ | 54-56 |
| 40226 | 2 | $-CH_2-CH\begin{smallmatrix}CH_3\\CH_3\end{smallmatrix}$ | 2 | $-N$(cyclohexyl)$_2$ | 139-140 (isopropylic ether) |
| 40453 | 4 | $-CH_2-CH\begin{smallmatrix}CH_3\\CH_3\end{smallmatrix}$ | 2 | $-N\begin{smallmatrix}CH(CH_3)(CH_3)\\CH(CH_3)(CH_3)\end{smallmatrix}$ | 127-128 (isopropylic ether) |
| 40455 | 3 | $-CH_2-CH\begin{smallmatrix}CH_3\\CH_3\end{smallmatrix}$ | 2 | $-N\begin{smallmatrix}CH(CH_3)(CH_3)\\CH(CH_3)(CH_3)\end{smallmatrix}$ | 110-111 (isopropylic ether) |

PROVING THE ANTIARRHYTHMIC PROPERTIES

Protocole:

The anti-arrhythmic power of these molecules was measured on an animal specimen of ventricular arrhythmia.

Mongrel dogs are anaesthetized and a metal spire is placed by retrograde catheterization in the coronary bed. At the same time, a frequency modulator micro transmitter is fixed on the back of the animal and connected to two precordial electrodes.

The animal once returned to its box shows signs of progressive thrombosis of the anterior interventricular artery. Thus a localized and transmural infarctus of the myocardium has declared itself, which is generator of an abnormal although repetitive electrical activity: ventricular tachycardia.

In this condition, the drugs are administered per os and the telemetered system permits to follow in real time the evolution of the dysrhythmia.

A count-up of the sino-auricular and pathological systolic complexes is ensured permanently by electronic processes, thereby permitting to quantify the quality and duration of activity of the products.

Results:

The results relative to the different products are given in Table 2.

The activity of the products tested on ventricular tachycardia is expressed either by the restoring of the sino-auricular rhythm, or by a considerable improvement of the ratio:

$$\frac{\text{number of abnormal complexes}}{\text{number of sino-auricular complexes}}$$

TABLE 2

| Products No. CM | Dose mg/kg P.O. | Number of Animals | Effect on Ventricular Tachycardia |
|---|---|---|---|
| CM 7526 | 50 | 3 | Sino-auricular Rythm or improvement at 90% from 3 h 15 to over 4 h 30 |
| CM 7641 | 50 | 2 | Sino-auricular Rythm or improvement between 70-90% from 1 h 45 to 6 hours. |
| CM 7827 | 50 | 1 | Improvement at 75% for 4 hours. |
| CM 7828 | 50 | 2 | Improvement between 60 and 95% from 2 h 30 to 5 hours. |
| CM 7855 | 50 | 3 | Sino-auricular Rythm or improvement at 80% from 30 mins. to 3 |

TABLE 2-continued

| Products No. CM | Dose mg/kg P.O. | Number of Animals | Effect on Ventricular Tachycardia |
|---|---|---|---|
| | | | hours. |
| CM 7857 | 50 | 3 | Sino-auricular Rythm or improvement at 85% from 3 hrs. to over 4 h 30. |
| CM 40023 | 50 | 5 | Improvement between 50 and 100% from 1 hr. to 2 h 45. |
| CM 40156 | 50 | 2 | Improvement 50% from 1 hr. to 2 hrs. |

In humans, the administration by oral route of a single dose of 50 mg of CM 7857 leads to the restoring of the sino-auricular rhythm.

PROVING THE BLOOD-PLATELETS ANTI-AGGREGANT PROPERTIES

Protocole:

The anti-aggregant power was measured in vitro and ex-vivo according to Born's turbidimetrical technique.

The tests in vitro were conducted on a platelet-rich plasma of human origin. The product to be tested is extemporaneously dissolved in an isotonic solution of sodium chloride. The product is incubated at 37° C. for 5 minutes in the presence of platelet-rich plasma before the addition of the aggregant agent.

The tests ex-vivo were conducted on a baboon subjected to a water diet on the day before the test. The product to be tested was administered orally in the dose of 50 mg/kg. Blood samples were taken before the administration of the product and then, 1,2,3 and 24 hours after the administration to analyze the aggregation of the platelets.

The results are given in percent of platelet aggregation inhibition calculated with respect to controls (aggregation at 100%).

Results:

The test in vitro conducted on a platelet-rich human plasma showed that the CM 7857 could antagonize the platelet aggregation induced by the collagen. The concentration necessary to inhibit by 50% the platelet aggregation is close to 80 μm.

The tests ex-vivo were conducted after oral administration of one dose of 50 mg/kg to 4 baboons. For that dose, an inhibition of 30% was observed vis-a-vis the platelet aggregation induced by the ADP.

In humans, the oral administration of one dose of 50 mg/kg of CM 7857 has cleared the disorders caused by the aggregation of platelets.

These results show that the products according to the invention have a strong action on dysrhythmia. They also have a considerable activity as platelets anti-aggregants.

Consequently, the products (I) can be used in human therapeutics as myocardium protectors to correct ventricular rhythm disorders of ischemic origin, as well as disorders caused by the aggregation of blood-platelets.

The products can be in the galenic forms corresponding to the oral route of administration (tablets, gelules, . . . ) and to the parenteral route of administration (ampules for injection).

The dose necessary for a blood-platelet anti-aggregant activity or for restoring the sino-auricular rythm in humans can vary between 400 and 800 mg approximately per day administered orally. Preferred dosage units for parenteral administration in humans varies between about 50 and about 150 mg. of active compound.

One example is the following galenic preparation:

| TABLETS | |
|---|---|
| CM 7857 | 0.200 g |
| Microcrystalline cellulose | 0.140 g |
| Lactose | 0.140 g |
| Magnesium stearate | 0.020 g |
| | 0.500 g |

What is claimed is:

1. A compound of the formula:

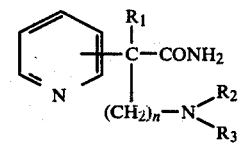

wherein:
the floating moiety is substituted in the 2-, 3- or 4-position of the ring;
$R_1$ is alkyl, or alicyclic or 1 to 10 carbon atoms;
$R_2$ and $R_3$ are alkyl or alicyclic of 1 to 6 carbon atoms, or $R_2$ and $R_3$, together with the nitrogen to which they are bonded, form a piperidine or morpholine unsubstituted or substituted by methyl; and
n is 2, 3 or 4.

2. A compound of claim 1 wherein $R_1$ is branched alkyl of 3 to 6 carbon atoms.

3. A compound of claim 1 wherein the alicyclic is an alicyclic of 6 or 7 carbon atoms.

4. A compound of claim 1 wherein: $R_1$ is

5. A compound of claim 1 wherein: $R_1$ is

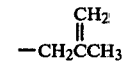

6. A compound of claim 1 wherein $R_1$ is alkyl of 2 to 5 carbon atoms.

7. A compound of claim 1 wherein: $R_1$ is

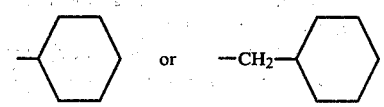

8. A compound of claim 1, 3, 6 or 7 wherein $R_2$ and $R_3$ are alkyl of 1 to 6 carbon atoms or alicyclic of 6 carbon atoms.

9. A compound of claim 1, 3, 6 or 7 wherein $R_2$ and $R_3$ are each

10. A compound of claim 1, 3, 6 or 7 wherein $R_2$ and $R_3$ together form

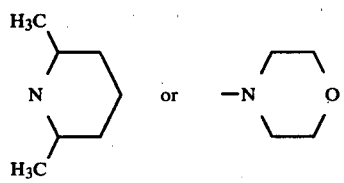

11. A compound of claim 1, 3, 6 or 7 wherein $R_2$ and $R_3$ are alkyl of 2 to 4 carbon atoms.

12. A compound of the formula:

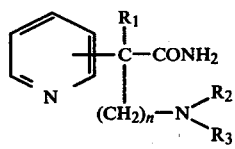

wherein:
the floating moiety is substituted in the 2-, 3- 4-position of the ring;
$R_1$ is alkyl, alkenyl, alkynyl or alicyclic of 1 to 10 carbon atoms;
$R_2$ and $R_3$ are branched alkyl of 3 to 6 carbon atoms, alicyclic of 1 to 6 carbon atoms, or together with the nitrogen to which they are bonded, form a morpholino or dimethyl-2,6-piperidino; and
n is 2, 3 or 4.

13. A compound of claim 12 wherein the $R^2$ is morpholino or dimethyl-2,6-piperidino.

14. Method for preparing the pyridine derivatives claimed in claim 1 or 12, in which derivatives the radical $R_1$ is a saturated alkyl or an alicyclic group, method consisting in the following successive steps:

(a) an acetonitrile pyridyl of formula:

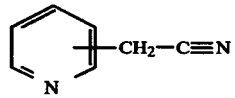

is treated with an aldehyde or a ketone of formula $R_4COR_5$, wherein $R_4$ is H or alkyl and $R_5$ is alkyl, the reaction taking place in the presence of acetic acid and piperidine in a solvent medium;

(b) the ethylenic nitrile resulting from the preceding reaction is reduced catalytically so as to obtain a saturated nitrile, the said reduction being conducted in known manner;

(c) The saturated nitrile obtained is subjected to an alkylation reaction with a compound of formula

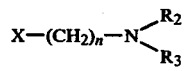

X being halogen;
(d) then the nitrile function of the product of the above reaction is hydrolyzed in manner known per se, to obtain the corresponding amide.

15. Method for preparing the pyridine derivatives of claim 1 or 12, in which derivatives the radical $R_1$ is a non-saturated alkyl radical, which method consists in:

(a) subjecting an acetonitrile pyridyl of formula:

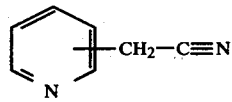

to an alkylation reaction with a compound of formula

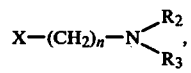

X being halogen
(b) subjecting the resulting product to a second alkylation reaction with a compound of formula $R_1X$ wherein $R_1$ is a non-saturated alkyl radical
(c) in hydrolyzing, in known manner, the nitrile function of the product obtained so as to arrive at the corresponding amide.

16. A method of treating arrhythmia in a patient suffering therefrom which comprises administering to the patient an effective antiarrhythmic amount of the compound of claim 1.

17. A method of treating aggregation of blood platelets in a patient in need thereof which comprises administering an effective antiaggregant amount of the compound of claim 1.

18. A pharmaceutical composition containing as an active ingredient an effective anti-arrhythmic amount of the compound of claim 1.

19. A pharmaceutical composition containing as an active ingredient an effective blood platelet antiaggregant amount of the compound of claim 1.

20. The pharmaceutical composition of claim 18 wherein the composition is in a form suitable for oral administration and the active ingredient is contained in an amount of from 400 to 800 mg.

21. The pharmaceutical composition of claim 19 wherein the composition is in a form suitable for oral administration and the active ingredient is contained in an amount of from 400 to 800 mg.

22. The pharmaceutical composition of claim 18 wherein the composition is in a form suitable for parenteral administration and the active ingredient is contained in an amount between about 50 mg and about 150 mg.

23. The pharmaceutical composition of claim 19 wherein the composition is in a form suitable for parenteral administration and the active ingredient is contained in an amount between about 50 mg and about 150 mg.

* * * * *